United States Patent
Ben Ishay et al.

(10) Patent No.: US 10,813,578 B1
(45) Date of Patent: Oct. 27, 2020

(54) SENSOR DEVICE FOR OPTICAL MEASUREMENT OF BIOLOGICAL PROPERTIES

(71) Applicant: BIOBEAT TECHNOLOGIES LTD., Petach Tikva (IL)

(72) Inventors: Arik Ben Ishay, Zoran (IL); Israel Sarussi, Ganei Tal (IL); Johanan May, Petach Tikva (IL)

(73) Assignee: BIOBEAT TECHNOLOGIES LTD., Petach Tikva (IL)

( * ) Notice: Subject to any disclaimer, the term of this patent is extended or adjusted under 35 U.S.C. 154(b) by 0 days.

(21) Appl. No.: 16/726,976

(22) Filed: Dec. 26, 2019

(51) Int. Cl.
*A61B 5/1455* (2006.01)
*A61B 5/024* (2006.01)
*A61B 5/021* (2006.01)

(52) U.S. Cl.
CPC ........ *A61B 5/1455* (2013.01); *A61B 5/02141* (2013.01); *A61B 5/02438* (2013.01); *A61B 5/02444* (2013.01)

(58) Field of Classification Search
CPC .............. A61B 5/1455; A61B 5/02438; A61B 5/02444; A61B 5/02141
See application file for complete search history.

(56) References Cited

U.S. PATENT DOCUMENTS

| | | | | |
|---|---|---|---|---|
| 6,134,458 A | * | 10/2000 | Rosenthal ............ | A61B 5/0059 600/310 |
| 2006/0079789 A1 | * | 4/2006 | Lee ...................... | A61B 5/0059 600/473 |

* cited by examiner

*Primary Examiner* — Eric F Winakur
*Assistant Examiner* — Abid A Mustansir
(74) *Attorney, Agent, or Firm* — Alphapatent Associates, Ltd; Daniel J. Swirsky

(57) ABSTRACT

A device, a substrate including a connection port. The substrate includes traces to enable a circuit of the substrate. The circuit is connected to the connection port. A light sensor mechanically and electrically attached respectfully to a first planar surface of the substrate and the circuit. A light source is mechanically and electrically attached respectively to the first planar surface and the circuit. The light source is located lateral to the light sensor at a first distance. A light signal of the light source emanates from the light source at an angle perpendicular to the first planar surface and a reflector mechanically attached to the first planar surface and located between the light sensor and the light source. The light signal is substantially reflected by the reflector away from the light sensor.

14 Claims, 12 Drawing Sheets

SENSOR DEVICE FOR OPTICAL MEASUREMENT OF BIOLOGICAL PROPERTIES

FIELD

The invention is generally in the field of optical measurement of biological properties of an examined subject, and to an optical measurement of blood related parameters of the examined subject. In particular the invention relates to a structure for a device to enable reflective blood measurement of certain features of the optical measurement detected by a detector. The structure improves the signal to noise ratio of the optical measurement detected by the detector.

BACKGROUND

The majority of optical blood pulse measurements (e.g., pulse oximetry) may be carried out utilizing transmissive measurement techniques requiring sensor devices that are mountable over two opposite sides of a thin body part/organ (e.g., fingertip or earlobe). In contrast to transmissive measurement techniques, reflective measurement techniques use a light source and a light detector which are on the same side of a tissue.

However, there are various advantages for reflective blood measurement techniques, which may be considered to be preferable in certain applications, particularly in types of wearable medical devices, such as medical watches or patches. Some of the advantages of reflective blood measurement techniques include, among other things, the ability to conduct optical measurements on almost any part of the body, including thick organs. Other advantages may be associated with the reduced energy consumption of reflective measurement techniques. The reduced energy consumption stems from the minimal energy required to reflect light from tissue layers, as opposed to transmissive techniques where the light is required to pass through the entire width of the organ.

There may be however various limitations associated with the reflective measurement techniques, such as low signal-to-noise ratios (SNR) and low AC/DC ratios. Alternating current (AC) in the light detector as a result of the light detection of the light wave signals reflected from (capillary) blood vessels may originate from the heart activity. Direct current (DC) in the light detector as a result of the light detection of the light wave signals may be a combination of light wave signals reflected from other parts of the examined organ tissue and light wave signals reflected directly from the organ surface which do not pass through the examined tissue.

Attempts to overcome limitations of reflective measurement techniques may include increasing the power of the irradiated light, by increasing the electrical current supplied to the light source and/or by increasing the number of light sources. Increasing the power of radiated light and/or increasing the number of light sources may also result in a respective increase of noise components in the measured light signals. The respective increase of noise components in the measured light signals may be due to respective increase of the baseline DC component and thus may not provide satisfying results. There is therefore a need to improve the quality of optical signals measured by reflective blood measurements techniques, to provide higher AC/DC ratios and improve the signal-to-noise ratios of the measured light signals.

SUMMARY

The invention, in embodiments thereof, discloses a structure for a sensor device designed for optical measurement of biological properties of a subject employing a reflective measurement technique. The reflective measurement techniques may be useful for measuring blood properties (e.g., heart rate, blood parameters and/or blood analyses concentration/level) in a living tissue of the examined subject. The optical measurement sensor device and its structure disclosed herein, overcome the deficiencies associated with the conventional measurement setups by including in the structure, reflection of the incident light of one or more light emitters by a reflector positioned in proper angle and distance relative to a light detector unit of the sensor device. Proper selection of the direction and distances of the one or more light sources relative to the light reflector (or one or more light reflectors relative to the light emitter) substantially improves the magnitudes, the SNR and the AC/DC ratios, of the measured optical signals.

Optical signals measured by reflective measurement techniques can be substantially improved by properly setting a distance between a light emitter and a light detection unit of the device, and an angle between their light detector and reflected light illumination directions. In this way most of the light components reaching the light detector are reflected/scattered from perfused layers of the illuminated tissue (also referred to herein as remote tissue layers), and that most of the light components reflected/scattered from non-perfused layers of the illuminated tissue (also referred to herein as near-surface tissue layers) do not reach the detector, and thus not measured.

Therefore, embodiments of the invention provide that the majority of the light components detected by the light detection unit are scattered from tissue layers comprising blood vessels, and therefore contain more information about the blood flowing through the examined tissue (i.e., the pulsating alternating current (AC) in the light detector as a result of the light detection. On the other hand, since many of the light components reflected/scattered from non-perfused tissue layers do not reach the detector and therefore not measured, the direct current (DC) in the light detector as a result of the light detection of the light signals measured is substantially reduced, which provides for substantial increase of the SNR and the AC/DC ratios of the measured signals.

In possible measurement setups of the measurement device, according to some possible embodiments, at least one light emitter and the structure of the device is used to emit light of one or more predetermined wavelength ranges over an examined tissue. At least one adjacently located light detector is used to detect light radiation of the one or more predetermined wavelength ranges reflected from the illuminated tissue. The at least one light emitter and the at least one light detector are arranged in a spaced apart relationship to attain certain distances therebetween to attain a certain angle between their respective illumination and detection directions.

In some embodiments of the device configuration disclosed herein, the certain distances and predefined orientations between the light emitter(s) and light detector(s) of the reflective measurement device are configured such that only light components within a predetermined range of angular reflections can reach the light detector and contribute to the measured optical signals. The configuration of the device by way of its structure thereby reduces, or in some cases, substantially prevents, collection of light components directly reflected from the organ surface (e.g., stratum corneum) without passing through any layer of the examined tissue, and/or reflected scattered light components from non-perfused upper layers of the examined tissue, and the like. The above two components (directly surface reflection and non-perfused upper layers reflection) are the main DC components. Thereby, a reduction at those components directly increases the AC/DC ratio. In some other exemplary embodiments of the invention the reflective measurement device and its structure may be configured to increase the light emission. Such configuration can extend the optical path of the emitted light in a given tissue layer, thereby increase the light scattering, and enhance the probability to collect light components reflected from the perfused tissue layer.

In some possible embodiments, the reflective measurement device may comprise a plurality of light emitters (e.g., 2, 3 or 4, or more) arranged around a light detector. The light emitted from each of the light emitters is reflected away from the direction of the light detector. It is however noted that in some embodiments, the reflective measurement device can be configured with acceptable good results using a single light emitter. In addition, in possible embodiments of the invention, several light detectors may be used to collect the light components reflected from examined tissue as the direction and distance of the light emitters relative to the light detectors of the device may be within acceptable ranges of the certain distances and predefined directions of the measurement device.

Embodiments of the invention may be used to implement wearable devices to be worn over a portion of body segments of a subject, such as, but not limited to, chest patch, head neck, torso, or limbs (e.g., over the wrist, like a watch).

The biological properties measured by the measurement device of the invention may comprise heart rate, blood flow, arterial blood oxygen saturation, and various blood related parameters such as concentration of a substance/analyte (e.g., sugar, cholesterol, hemoglobin, bilirubin) in blood, cardiac parameters, and the like. Thus, in some possible embodiments, the light emitter is configured to illuminate the examined tissue with multiple wavelengths selected for enabling determination of one or more biological properties of the subject.

In one embodiment a device is provided having a substrate including a connection port. The substrate includes traces to enable a circuit of the substrate. The circuit is connected to the connection port. A light sensor is mechanically and electrically attached respectfully to a first planar surface of the substrate and the circuit. A light emitter is mechanically and electrically attached respectively to the first planar surface and the circuit. The light emitter is located lateral to the light sensor at a first distance. The light emitter emits a light signal at an angle perpendicular to the first planar surface, said light signal is reflected by a reflector mechanically attached to the first planar surface and located between the light sensor and the light emitter. The light signal is substantially reflected by the reflector away from the light sensor. A profile of a cross section of the reflector is at least one of a linear profile, a concave profile, convex profile and a parabolic profile.

The first distance between the light emitter and a light emitter may be established responsive to the contours of the reflector reflecting the light emitted by the light emitter. The light emitter may include a lens configured to collimate the light signal of the light emitter at an angle perpendicular to the first planar surface. The light emitter may include an offset lens configured to collimate the light signal of the light emitter at a second angle away from an angle perpendicular to the first planar surface. The light emitter may include a lens configured to polarize the light signal of the light emitter. The light emitter may include a prism configured to reflect the light signal of the light emitter.

The device may further include a second reflector configured to reflect light emitted from a second light emitter. The second light emitter is mechanically and electrically attached respectively to the first planar surface and the circuit. A second light signal of the second light emitter emanates from the second light emitter at an angle perpendicular to the first planar surface. The second light signal is substantially reflected by the second reflector away from the light detector. A second distance between the light detector and the second light emitter may be established responsive to the contours of the second reflector.

A second planar surface of the reflector is placeable on an examined tissue to measure a biological property of an examined tissue. The second planar surface is parallel to the first planar surface. The device may further include an attachment device to enable attachment of the device to the examined tissue. The examined tissue is in contact with the second planar surface of the reflector.

The device may further includer a control unit operatively connected to the substrate and configured to select a parameter the light signal and/or the second light signal applied to the examined tissue. The parameter may be a wavelength and/or light intensity. The control unit may be configured to select and apply the light signal or the second light signal to the examined tissue. The control unit may also be configured to sense a reflected light signal from the light signal and/or the second light signal applied responsive to the parameter and/or respective first and second distances. The control unit may also be configured to receive and process a measurement data of the reflected light signal sensed by the light sensor to determine the biological properties of the examined tissue. The biological properties may include heart rate, oxygen saturation, hemoglobin level, blood pressure, cardiac output, stroke volume, perspiration, glucose/sugar level, bilirubin level or fat level.

BRIEF DESCRIPTION OF THE DRAWINGS

In order to understand the invention and to see how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings like reference numerals are used to indicate corresponding parts, and in which.

DETAILED DESCRIPTION

Figure 1:
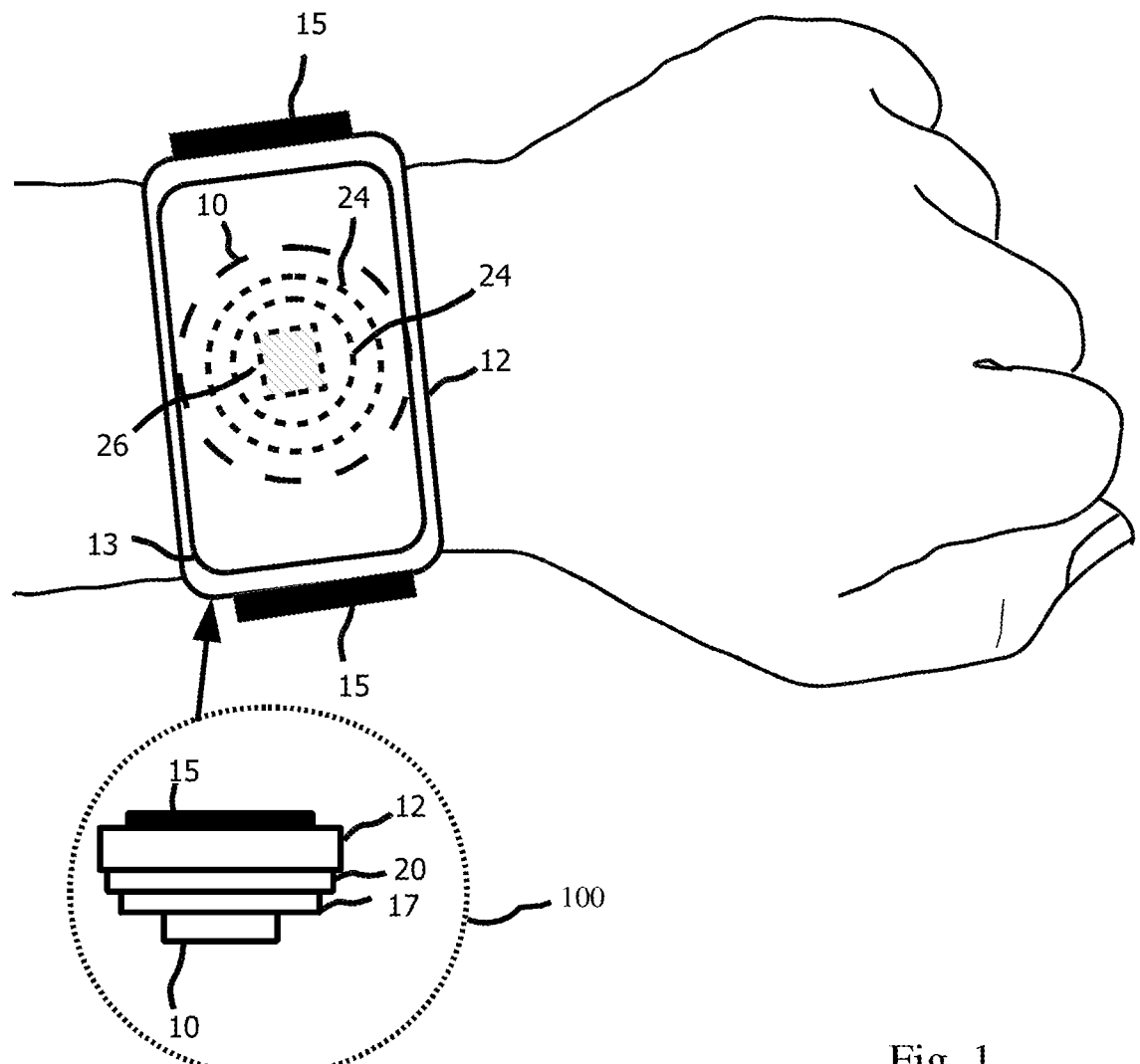
FIG. 1 shows an illustration of an application of a sensor device to an examined tissue, according to one or more illustrative aspects of the disclosure.

One or more specific embodiments of the present disclosure will be described below with reference to the drawings, which are to be considered in all aspects as illustrative only and not restrictive in any manner. In an effort to provide a concise description of these embodiments, not all features of an actual implementation are described in the specification. Elements illustrated in the drawings are not necessarily to scale, emphasis instead being placed upon clearly illustrating the principles of the invention. This invention may be provided in other specific forms and embodiments without departing from the essential characteristics described herein.

By way of introduction, the invention discloses an optical sensor device, whereby a structure of the optical sensor device provides illumination of an examined tissue with light signals that travel laterally away from a light detector included in the optical sensor device. Features of the structure enable magnitudes of reflected optical signals to be measured from the examined tissue with SNR and AC/DC ratios of the reflected optical signals to be significantly improved.

It is noted that the reflective measurement techniques and a structure of a sensor device disclosed herein are also useful for mitigation of optical signal distortions that may be induced in the measured signals of the light detector due to movements of the body part/organ to which the sensor device is attached.

The techniques disclosed herein are applicable to almost any type of optical measurements of blood properties, parameters and/or analytes, employing effects of optical absorption and scattering of electromagnetic radiation in a living tissue. Particularly, the techniques disclosed herein are useful for measuring pulsating signals, as typically obtained in types of non-invasive blood measurements, such as, but not limited to, pulse oximetry, Photoplethysmography (PPG) measurements, and the like. For example, and without being limiting, the optical measurement techniques disclosed herein may be useful for measuring blood pulses, oxygen ($O_2$) saturation, hemoglobin levels, glucose/sugar levels, bilirubin levels, and suchlike.

Reference is now made to FIG. 1, which shows an illustration of the application of a sensor device 10, according to one or more illustrative aspects of the disclosure. Sensor device 10 is an example of a reflective optical measurement device which is illustrated in further detail below. Sensor device 10 (shown by dashed line) is located on the underside of a housing 12 so that reflectors 24 (shown by dashed line) of sensor device 10 are in contact with the skin of a wrist of a user. Further located on the underside of housing 12 is a light detector 26 shown by hashed lines. Housing 12 on its upper surface includes a display 13. Housing 12 is shown as a watch arrangement where an adjustable strap 15 is used to attach the watch to the wrist of the user. A handle (not shown) may be attached to housing 12 to give a way to press the sensor device 10 onto a part of a body of the user.

A side view 100 of the underside of a housing 12 is shown where adjustable strap 15 is attached to housing 12, substrate 20 is operatively attached inside housing 12 both mechanically and electrically and may protrude away out from housing 12 and includes connection to a battery 17. Substrate 20 includes traces (not shown) which provides the electrical interconnections of the parts of sensor device 10 as well as connections to display 13, battery 17 and a microcontroller (not shown) for example. Sensor device 10 is both mechanically and electrically connected to housing 12, substrate 20 and battery 17.

Adjustable strap 15 may be tightened around the wrist to press sensor device 10 securely onto a part of the body of a person. The body part may be an ankle or around a torso of the person. Adjustable strap 15 may therefore, enable a biological property of an examined tissue of the person who is currently exercising or as a patient monitored over a longer period of time. The biological property may include heart rate, oxygen saturation, hemoglobin level, blood pressure, cardiac output, stroke volume, perspiration, glucose/sugar level, bilirubin level and fat level for example. The biological property may be displayed to the user on display 13.

Figure 2:
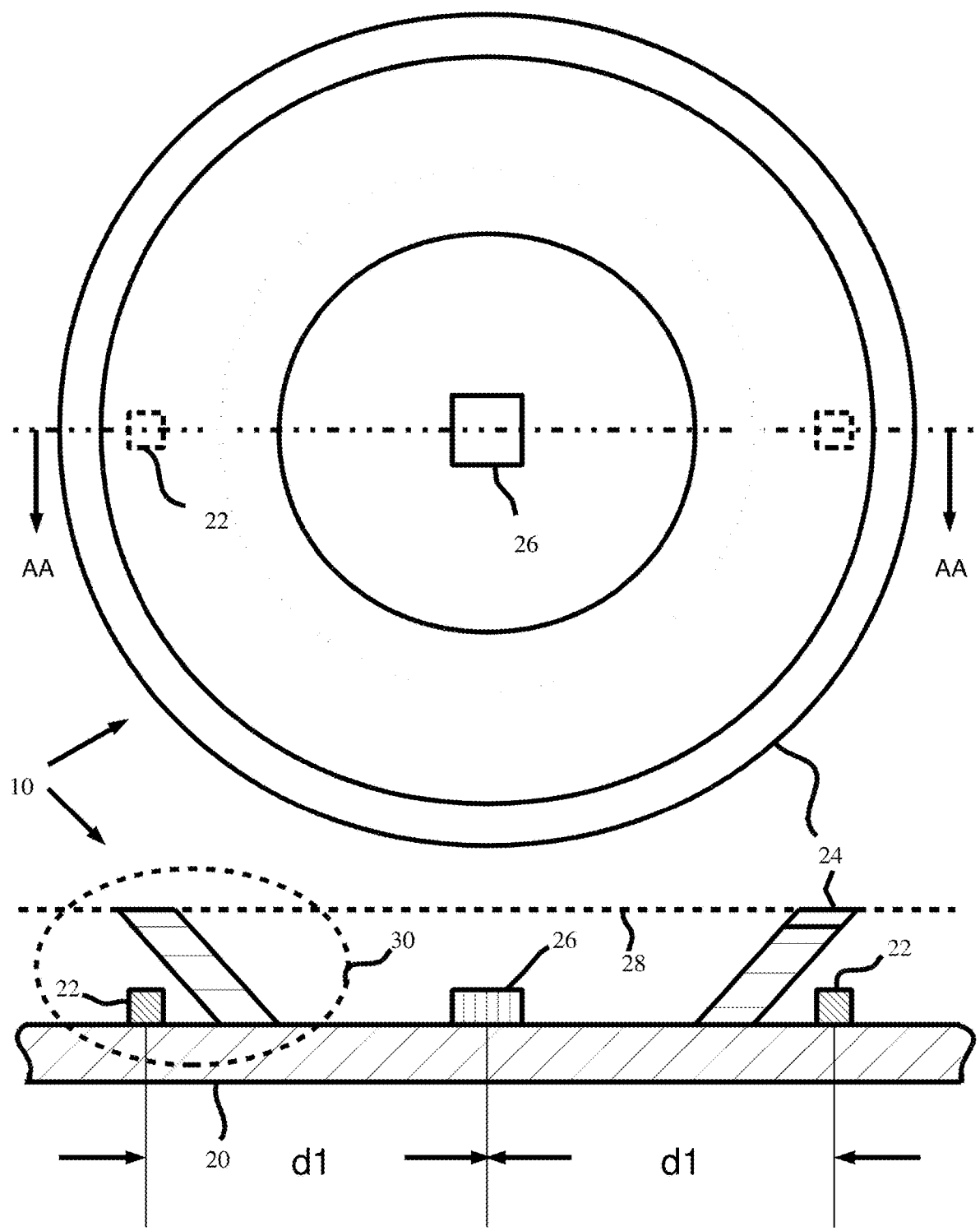
FIG. 2 shows a plan view and a side view cross-section of a sensor device, according to one or more illustrative aspects of the disclosure.

Reference is now made to FIG. 2 which shows a top view and a side view cross-section AA of sensor device 10, according to one or more illustrative aspects of the disclosure. The top view shows a reflector 24 mounted on substrate 20 shown partially in the side view cross-section AA. Light detector 26 is located in the centre of reflector 24. Area 30 (shown by dashed ellipse) in the side view cross-section and the top view shows how reflector 24 covers light emitter 22. Light emitter 22 are shown in the top view by dashed boxes. In the side view cross-section AA, light emitter 22 are both mechanically and electrically attached to the planar surface of substrate 20 with both positioned laterally at a distance d1 away from the centre of light detector 26. Dashed line 28 demonstrates how the planar surface of substrate 20 is parallel to the second planar surface of reflector 24. The second planar surface of reflector 24 of sensor device 10 is pressed onto an examined tissue in order to measure a biological property of the examined tissue. Reflector 24 is made of a material which is rigid enough so as not to be deformed as a result of sensor device 10 being pressed onto an examined tissue.

Figure 3A:
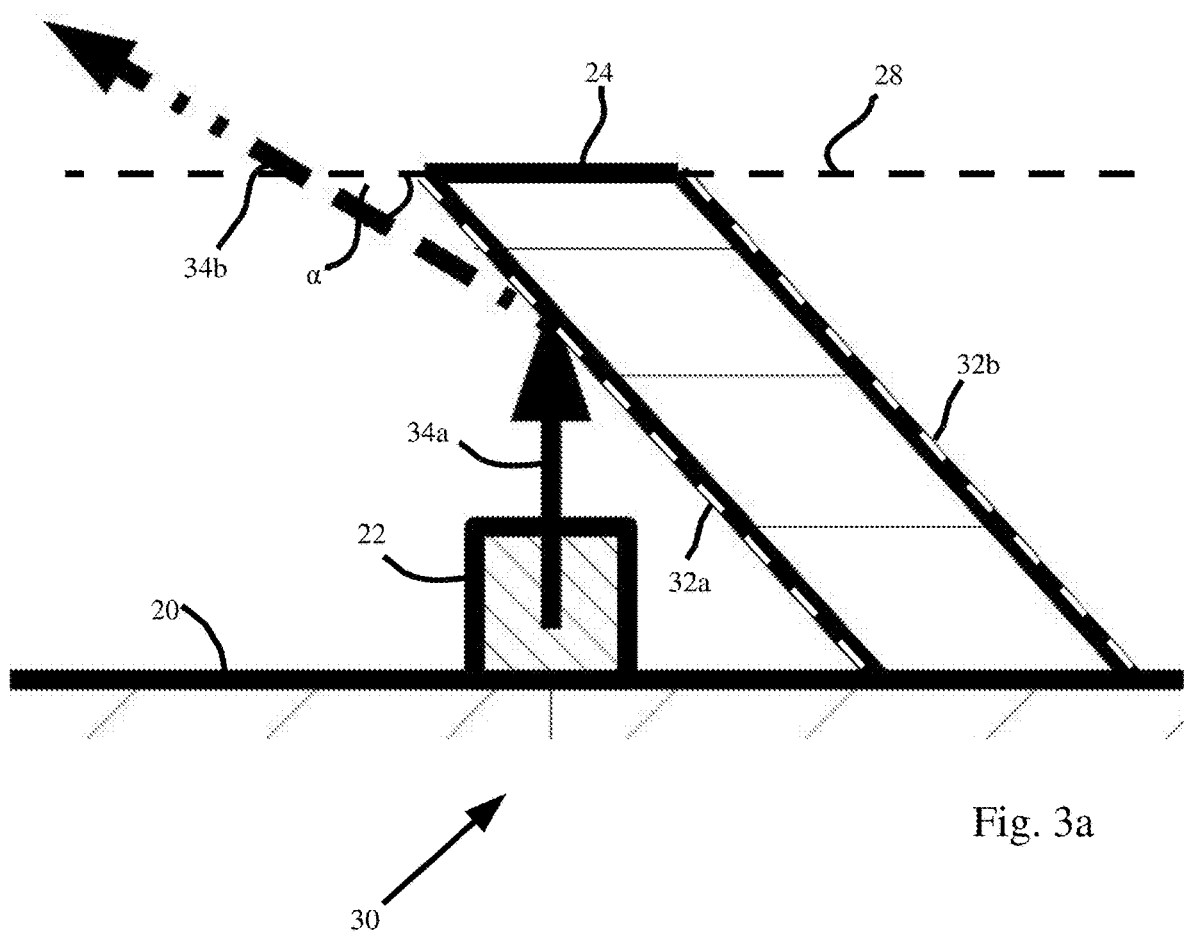
FIGS. 3a, 3b, 3c, 3d, 3e and 3f show more details of an area of a sensor device, according to one or more illustrative aspects of the disclosure.

Reference is now made to FIG. 3a which shows more details of area 30, according to one or more illustrative aspects of the disclosure. Area 30 shows reflective surfaces 32a and 32b of reflector 24. Reflective surfaces 32a and 32b of reflector 24 are examples of a linear shape in cross section AA. Light signal 34a emanates from light emitter 22 at an angle perpendicular to the first planar surface of substrate 20. Light signal 34a is reflected from reflective surface 32a as reflected light 34b at an angle α relative to dashed line 28. Light signal 34a is reflected away from light detector 26 (not shown).

Figure 3B:
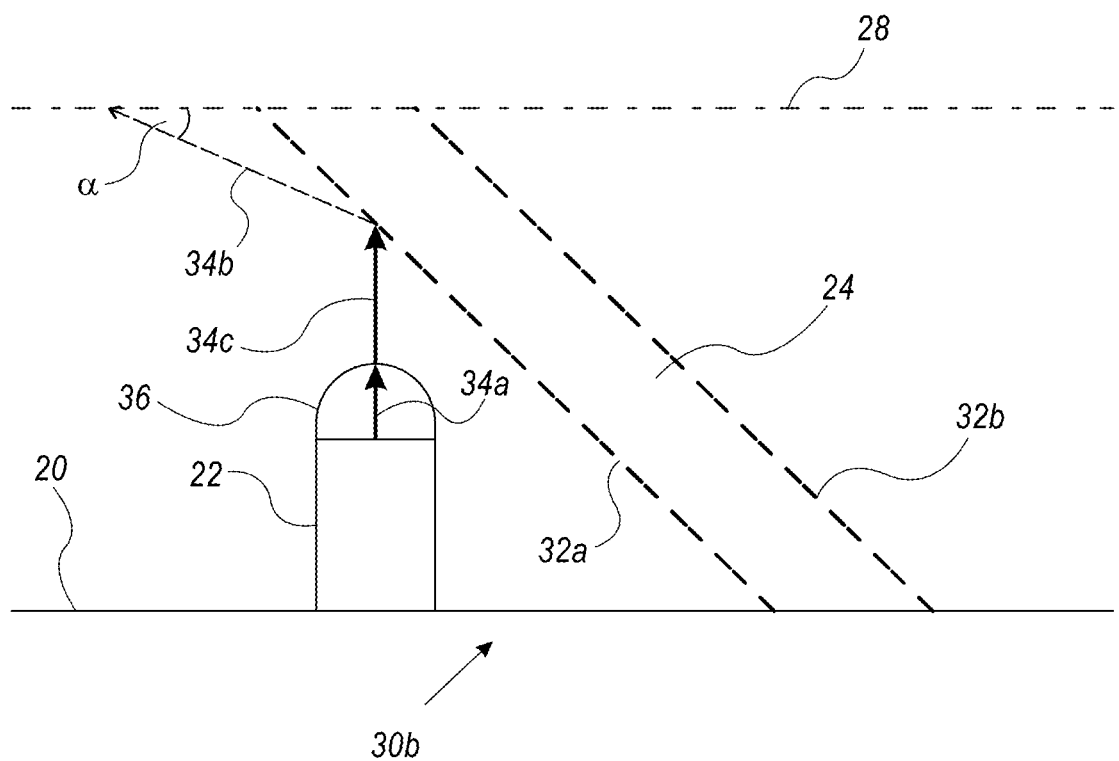

Reference is now made to FIG. 3b which shows an area 30b of sensor device 10, according to one or more illustrative aspects of the disclosure. FIG. 3b is the same as FIG. 3a except a lens 36 is shown placed on a distal end of light source 22. Light signal 34a still emanates from light source 22 at an angle perpendicular to the first planar surface of substrate 20. However, lens 36 causes light signal 34a to be collimated into collimated beam 34c. Collimated beam 34c minimizes the spread of the rays of light signal 34a. Collimated beam 34c still emanates from lens 36 at an angle perpendicular to the first planar surface of substrate 20. Collimated beam 32c is reflected from reflective surface 32a of reflector 24 as reflected light signal 34b at an angle α relative to dashed line 28. Collimated beam 32c is reflected away from light detector 26 (not shown) as reflected light signal 34b. Lens 36 may also include a polarizing filter (not shown) which polarizes collimated beam 34c. Reflector 24 also includes reflective surface 32b. In some cases, the device may comprise a prism used to reflect collimated beam 32c away from light detector 26 instead of lens 36.

Figure 3C:
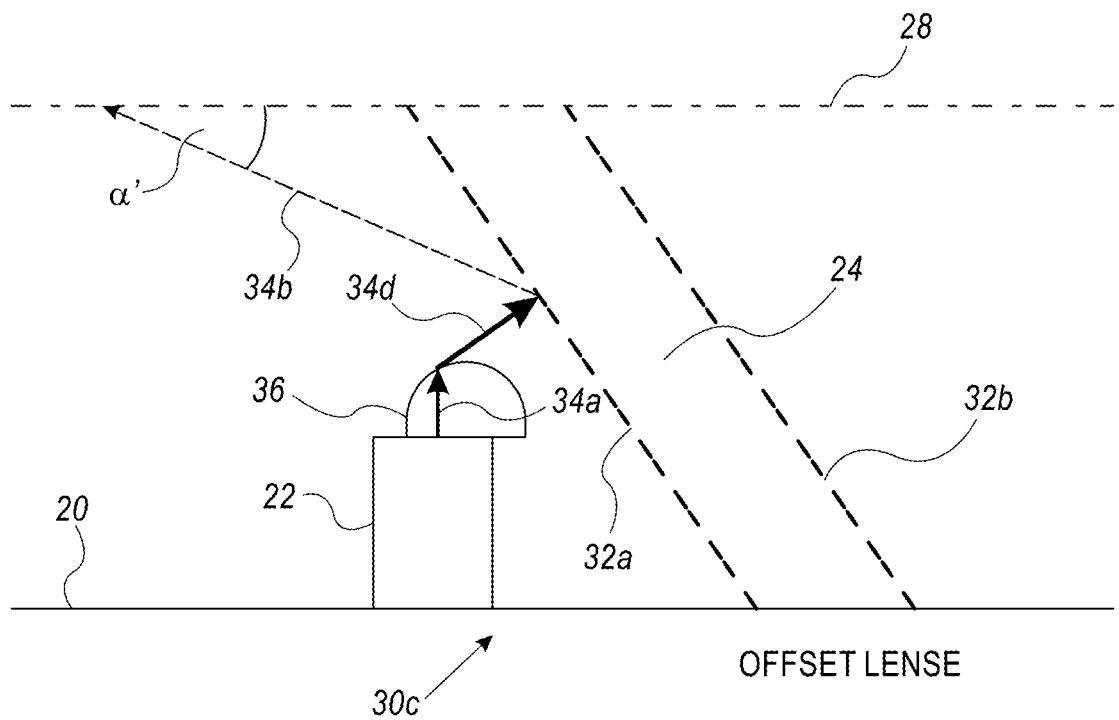

Reference is now made to FIG. 3c which shows an area 30c of sensor device 10, according to one or more illustrative aspects of the disclosure. FIG. 3c is the same as FIG. 3b, except lens 36 is placed on a distal end of light source 22 and offset laterally towards reflective surface 32a. Lens 36 may also be offset laterally further away from reflective surface 32a. Light signal 34a still emanates from light source 22 at an angle perpendicular to the first planar surface of substrate 20. However, unlike FIG. 3b, Lens 36 causes light signal 34a to be collimated into collimated beam 34d. Lens 36 minimizes the spread and/or scattering of the rays of light signal 34a. However, unlike FIG. 3b, collimated beam 34d is not at an angle perpendicular to the first planar surface of substrate 20. Collimated beam 34d is reflected from reflective surface 32a of reflector 24 as reflected light signal 34b at an angle α' relative to dashed line 28. Light signal 34a is reflected away from light detector 26 (not shown). Angle α' may be less acute than angle α reflective because lens 36 is offset laterally towards reflective surface 32a. Lens 36 may also include a polarizing filter (not shown) which polarizes collimated beam 34d. Reflector 24 also includes reflective surface 32b.

Figure 3D:
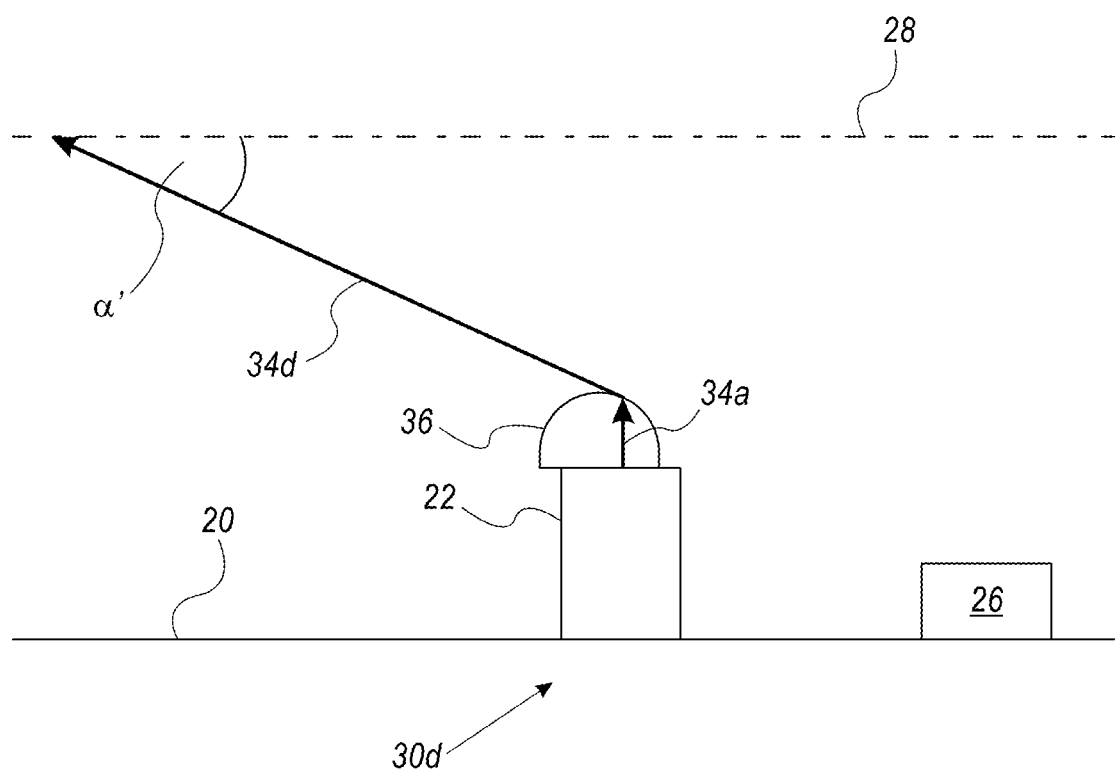

Reference is now made to FIG. 3d which shows an area 30d of sensor device 10, according to one or more illustrative aspects of the disclosure. FIG. 3d is the same as FIG. 3c, except lens 36 is placed on a distal end of light source 22 and offset laterally away from light detector 26. Light signal 34a still emanates from light source 22 at an angle perpendicular to the first planar surface of substrate 20. Lens 36 causes light signal 34a to be collimated into collimated beam 34d. Lens 36 minimizes the spread and/or scattering of the rays of light signal 34a. Collimated beam 34d is not at an angle perpendicular to the first planar surface of substrate 20. Collimated beam 34d is deflected away from light detector 26 (not shown) by virtue of lens 36 being offset laterally away from light detector 26. Angle α' may be less acute than angle α reflective because lens 36 is offset laterally away from light detector 26. Lens 36 may also include a polarizing filter (not shown) which polarizes collimated beam 34d. Area 30d of sensor device 10 is an example where the utilization of lens 36 does not require a reflector 24. Therefore, sensor device 10 may include multiple light sources 22 and respective lenses 36 without any reflectors 24. Another possibility is that sensor device 10 may include a combination of light sources 22 and reflectors 24, light sources 22/lenses 36 and reflectors 24, or light sources 22/lenses 36 and no reflectors 24.

Figure 3E:
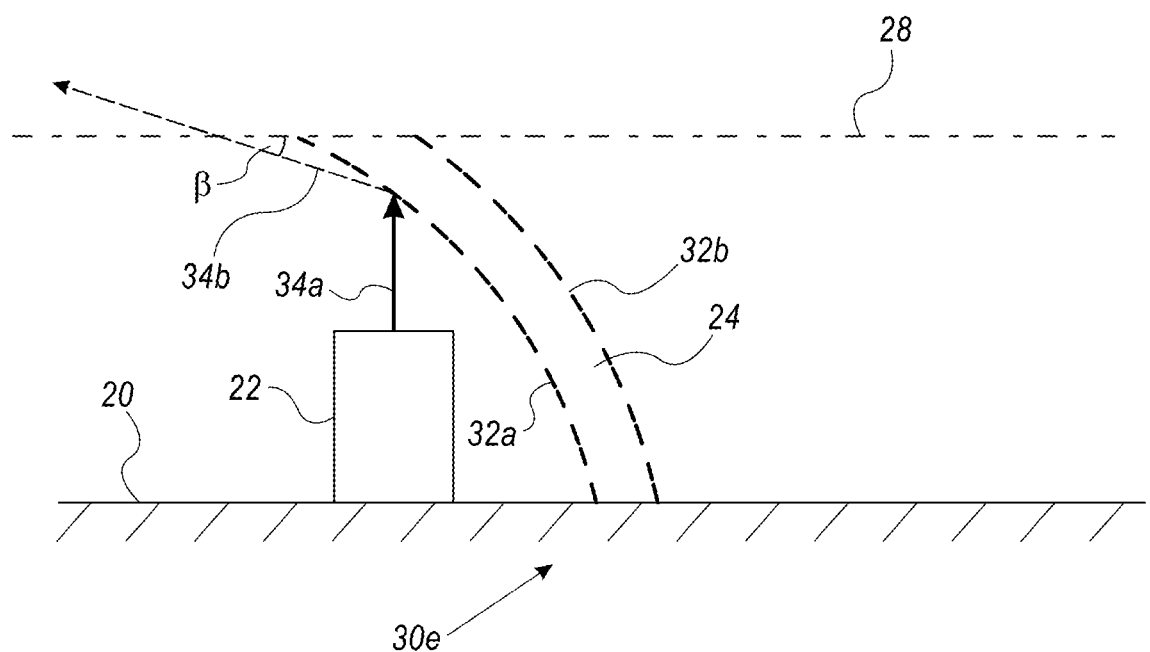

Reference is now made to FIG. 3e which shows area 30e of sensor device 10, according to one or more illustrative aspects of the disclosure. FIG. 3e is the same as FIGS. 3a, 3b and 3c, except reflector 24 is an example of being concave or parabolic in shape in cross section AA. Light signal 34a still emanates from light source 22 at an angle perpendicular to the first planar surface of substrate 20. Reflector 24 being concave or parabolic in shape reflects light signal 34a from reflective surface 32a to reflected light 34b at an angle β relative to dashed line 28. Angle β compared to angle α as shown in FIG. 3a, may be more acute by virtue of reflector 24 being concave or parabolic in shape in cross section AA. Reflector 24 also includes reflective surface 32b.

Figure 3F:
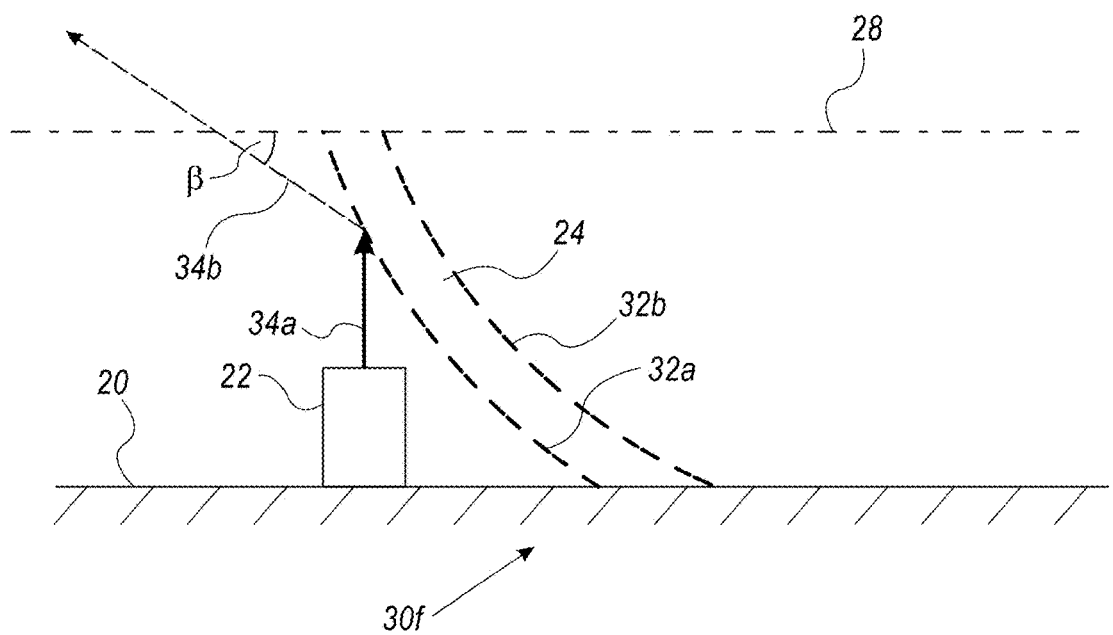

Reference is now made to FIG. 3f which shows area 30f of sensor device 10, according to one or more illustrative aspects of the disclosure. Reflector 24 is an example of being convex in shape in cross section AA. Light signal 34a still emanates from light source 22 at an angle perpendicular to the first planar surface of substrate 20. Reflector 24 being convex in shape at section AA reflects light signal 34a from reflective surface 32a to reflected light 34b at an angle β' relative to dashed line 28. Angle β' compared to angle β as shown in FIG. 3e, may be more acute by virtue of reflector 24 being convex in shape in cross section AA. Reflector 24 also includes surface 32b.

Figure 4:
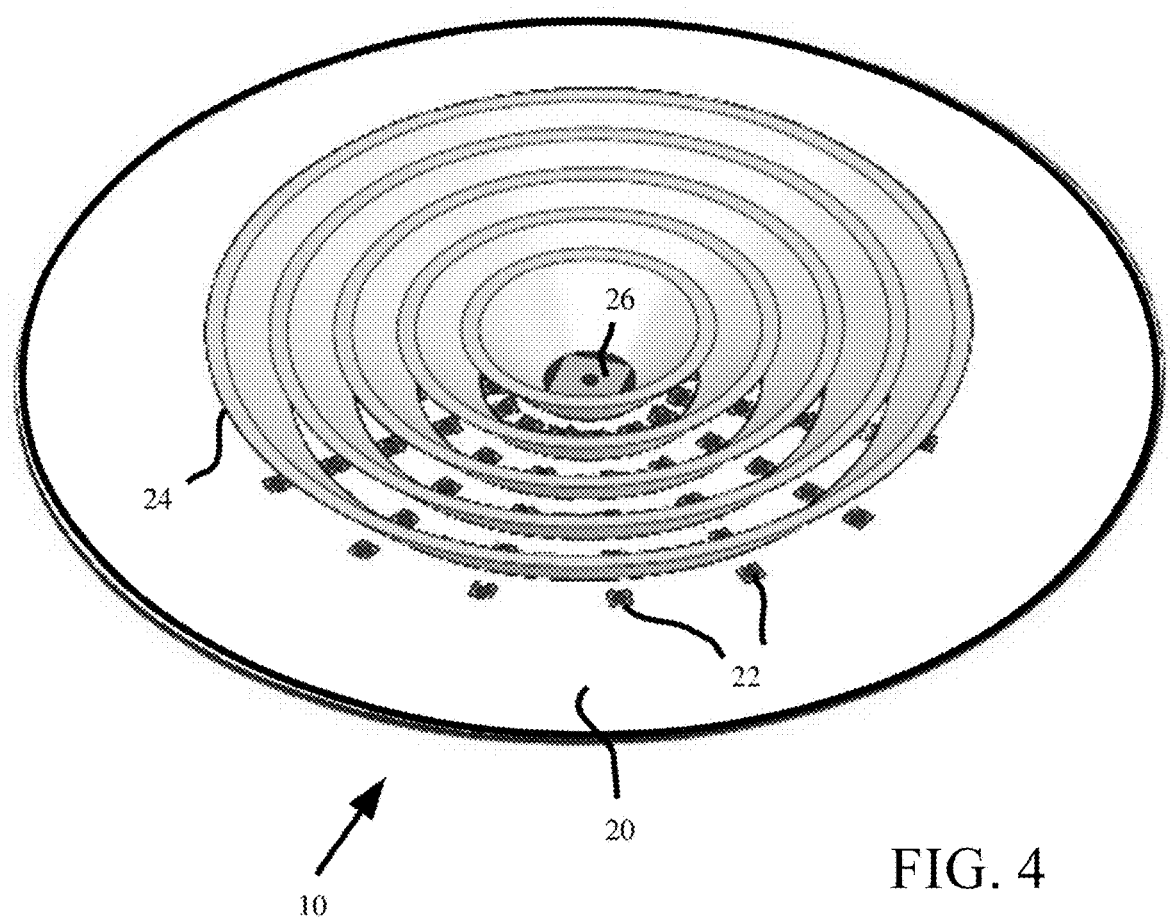
FIG. 4 shows a two-dimensional drawing of the underside of a sensor device, according to one or more illustrative aspects of the disclosure.

Reference is now made to FIG. 4 which shows a two-dimensional drawing of the underside of sensor device 10, according to one or more illustrative aspects of the disclosure. The underside of sensor device 10 shows a substrate 20. Substrate 20 may constitute a housing for sensor device 10 or may be included and operatively attached to a separate housing for sensor device 10. The housing or separate housing may additionally provide a, handle or the adjustable strap described above to enable sensor device 10 to be pressed onto a tissue. Substrate 20 also provides a mechanical attachment of multiple reflectors 24, light sources 22 and light detector 26 to substrate 20. Multiple reflectors 24 are shown concentric to each other at the center of the first planar surface of substrate 20 where light detector 26 is located.

Substrate 2.0 further provide an electrical attachment (not shown) to light sources 2.2 and light detector 26. The electrical attachment may include traces which provides the electrical interconnections of light sources 22 to each other, connections to light detector 26 and additional components which may connect to the electrical interconnections. Light sources 22 and light detector 26 are shown attached to the surface of substrate 20 but may located and attached below the surface. The additional components may include driver circuitries which may be utilized to set current levels, light intensities and wavelengths of the light signal which may emanate from light sources 22. The additional components may further include a microcontroller or microprocessor (not shown) which is connectable to the additional components and traces. The microcontroller may be utilized to select which light source 22 and/or light sources 22 is to be activated and applied responsive to which biological property part of the body and monitored by light detector 26. Further to perform an analysis of a biological property monitored by light detector 26, to store and display a datum of the analysis in a respective memory or a display such as display 13 which may be operatively attached to the microcontroller. The additional components may yet further include a connector to the microcontroller. The connector may be provided on the housing of sensor device 10 or sensor device 10 may provide a wireless connection to another computing device (cloud or server) to enable a remote analysis, storage and display of the datum.

Light sources 22 by way of non-limiting example may be multicolor light emitting diodes (LEDs). Multicolor LEDs typically have three selectable wavelengths of red light (wavelength[λ]≈670 nano-meters[nm]), blue (λ≈460 nm) and green (λ≈550 nm). White light may be by the microcontroller selecting red, blue and green wavelengths/color temperature by additional control of the LED driver circuitries. Selection by the microcontroller of which wavelength, color temperature and/or combination of wavelengths and color temperature may be responsive to different tissues in the human body, which have different levels of absorption and reflectivity. Levels of absorption and reflectivity may also be wavelength-dependent. Selection by the microcontroller of which light source 22, wavelength, color temperature and/or combination of wavelengths and color temperature may be further responsive to the distances of light sources 22 to light detector 26 as discussed in further detail in the descriptions which follow.

Figure 5A:
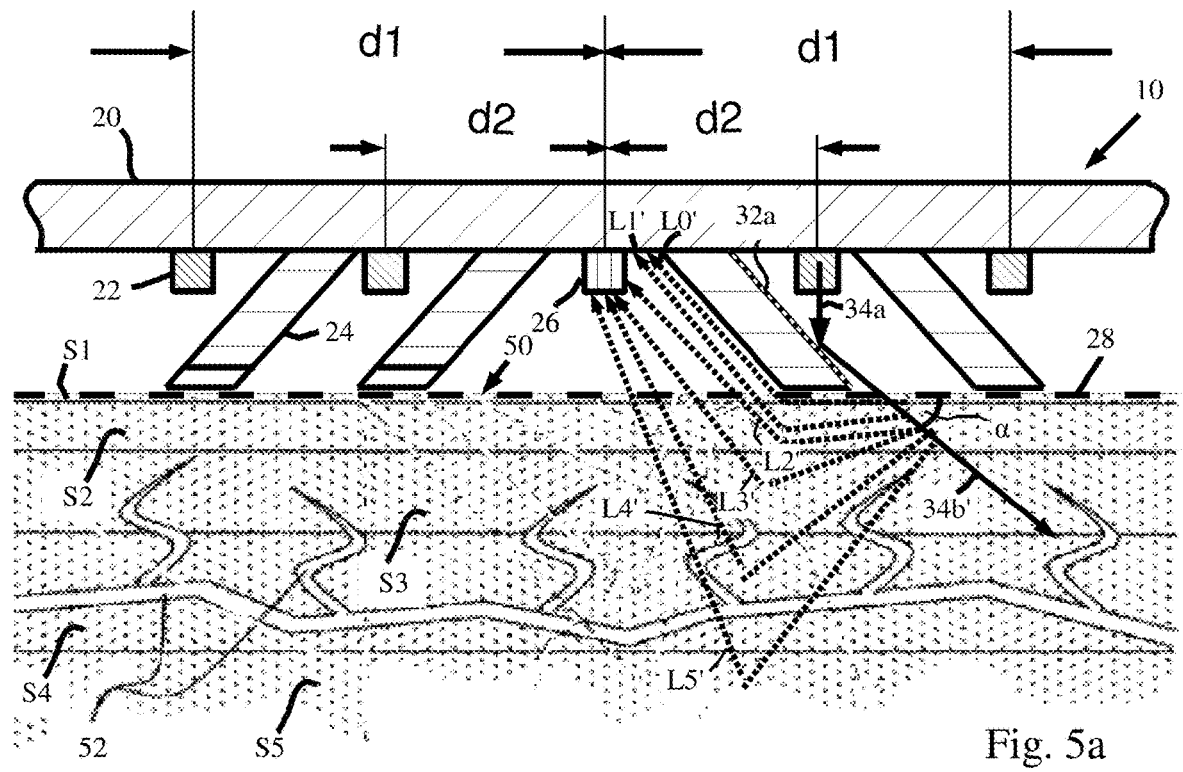
FIG. 5a shows a partial cross-sectional side view of a sensor device and its application to an examined tissue, according to one or more illustrative aspects of the disclosure.

Reference is now made to FIG. 5a which shows a partial cross-sectional side view of sensor device 10 and its application to a tissue 50, according to one or more illustrative aspects of the disclosure. Tissue 50 includes non-perfused near-surface tissue layers S1 and S2 which for example form the epidermis of the skin. Tissue 50 further includes remote perfused tissue layers, S3, S4 and S5 which may include blood vessels 16. Sensor device 10 is shown pressed against tissue layer S1 so that the second planar surface of reflectors 24 are in contact with tissue layer S1. Reflectors 24 in contact with tissue layer S1 is in order to enable a measurement of a biological property of tissue 50. The second planar surface of reflector 24 is in parallel with the first planar surface of substrate 20 and is indicated by dashed line 28. Four light sources 22 are shown.

For ease of explanation, one light source 22 is shown with light signal 34a emitted from the one light source 22. The one light source located laterally to the right of light detector 26 at a shorter distance d2 when compared to another light source 22 located laterally to the right of light detector 26 at a greater distance d1. Similarly, two other light sources 22 are also shown located laterally to the left of light detector 26. One of the two other light sources 22 located laterally to the left of light detector 26 is located at a shorter distance d2 when compared to the other of the two light source 22 at the greater distance d1. Light signal 34a from light source 22 is emitted perpendicular to both the first and the second planar surfaces. Light signal 34a is reflected off reflective surface 32a of reflector 24, as reflected light 34b' at an angle α relative to dashed line 28.

Angle α of the orientation of reflected light 34b' permits light source 22 to be located at a relative short distance d2 in the vicinity of the light detector 26. The relative short distance d2 in the vicinity of light detector 26 may guarantee that the light components L0', L1' and L2' of reflected light 34b', are reflected from the non-perfused tissue layers S1 and S2. The light direction towards light detector 26 may be perpendicular to both the first and the second planar surfaces. Thus, the number of light components L0', L1' and L2' reflected from the non-perfused near-surface tissue layers S1 and S2 towards the light detector 26 are reduced to give an improved SNR and AC/DC ratio. Where alternating current (AC) in light detector 26 may be as a result of the light detection of the light wave signals of light 34b' reflected from (capillary) blood vessels 16 which may originate from the heart activity. Where direct current (DC) in light detector 26 may be as a result of the light detection of the light wave signals of light 34b' reflected from other parts of tissue 50 and light wave signals reflected directly from the surface layers S1 and S2 which do not pass through tissue 50.

Direct current (DC) in the light detector as a result of the light detection of the light wave signals may be a combination of light wave signals reflected.

On the other hand, light components L3', L4' and L5', which are reflected from perfused tissue layers S3, S4 and S5 respectively, are caused to travel greater distances into tissue 50 until they are reflected towards the light detector 26. The greater distances traveled by light components L3', IA' and L5', are compared with respect to a light signal entering perpendicular to the surface of tissue 50. Therefore, by light components L3', L4' and L5' may interact with greater amounts of respective perfused tissue layers S3, S4 and S5 so that the amount of pulsating AC information they contain is substantially increased.

Figure 5B:
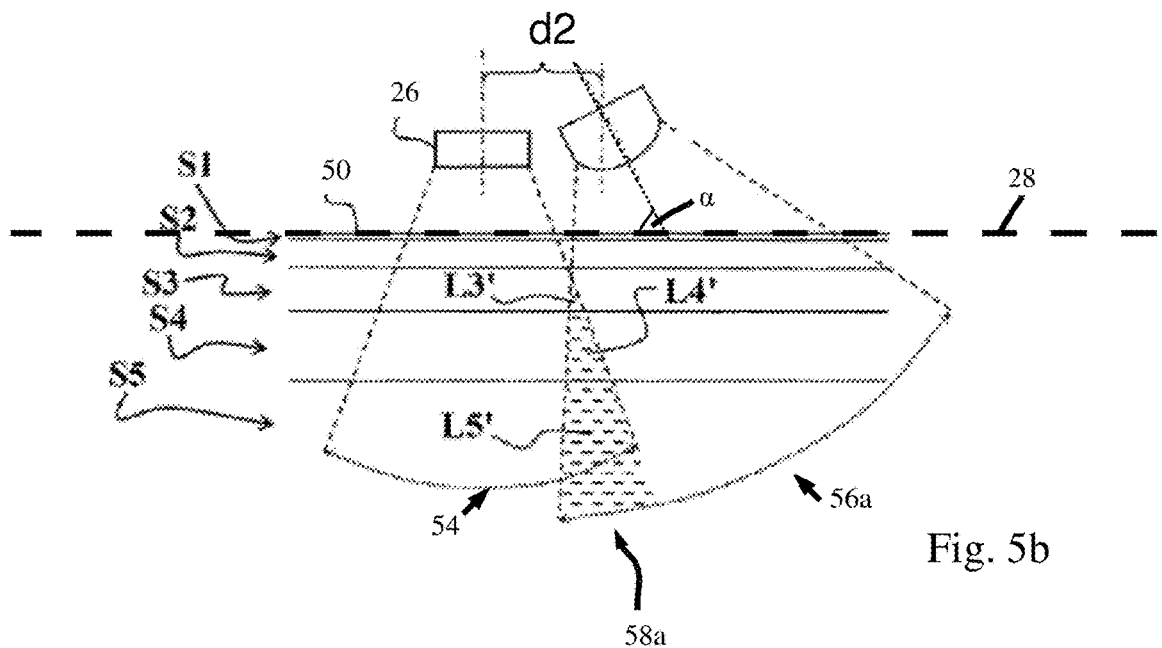
FIG. 5b shows a simplified schematic of FIG. 5a to illustrate features of an area of light interaction in perfused tissue layers, according to one or more illustrative aspects of the disclosure.

Reference is now made to FIG. 5b which shows a simplified schematic of FIG. 5a to illustrate features of an area of light interaction in perfused tissue layers S1-S5, according to one or more illustrative aspects of the disclosure. Area 58a (shown shaded) includes intersection of illumination sector 56a with perfused layers S3-S5 that coincides within a portion of sector 54. Illumination sector 56a is formed by light signal 34a (not shown) reflected off reflective surface 32a as reflected light 34b'. Light signals L3', L4' and L5' are reflected towards light detector 26 from perfused tissue layers S3, S4 and S5. The field of view of reception of received light signals of light detector 26 is indicated by sector 54. Light intersection area 58a in perfused tissue layers S3, S4 and S5 is therefore, dependent on angle α relative to dashed line 28, so that light components L3', L4' and L5' are reflected towards light detector 26 from perfused tissue layers S3, S4 and S5.

Accordingly, the baseline DC components in the optical signals measured by the light detector 26 in the reflective measurement are substantially reduced, by reducing the amount (or altogether excluding) of light components L0', L1' and L2', reflected from the non-perfused tissue layers S1 and S2 (shown in FIG. 5a). On the other hand, since the optical paths, of the light components L3', L4' and L5' reflected towards the light detector 26 from the perfused tissue layers are increased by virtue of angle α. The light components L3', and L5' indicate a more intense interaction with perfused tissue layers S3, S4 and S5. Thus, light components L3', L4' and L5' may contain significantly more blood related information and contribute greater amounts of pulsating AC components to the optical signals measured by light detector 26.

Figure 5C:
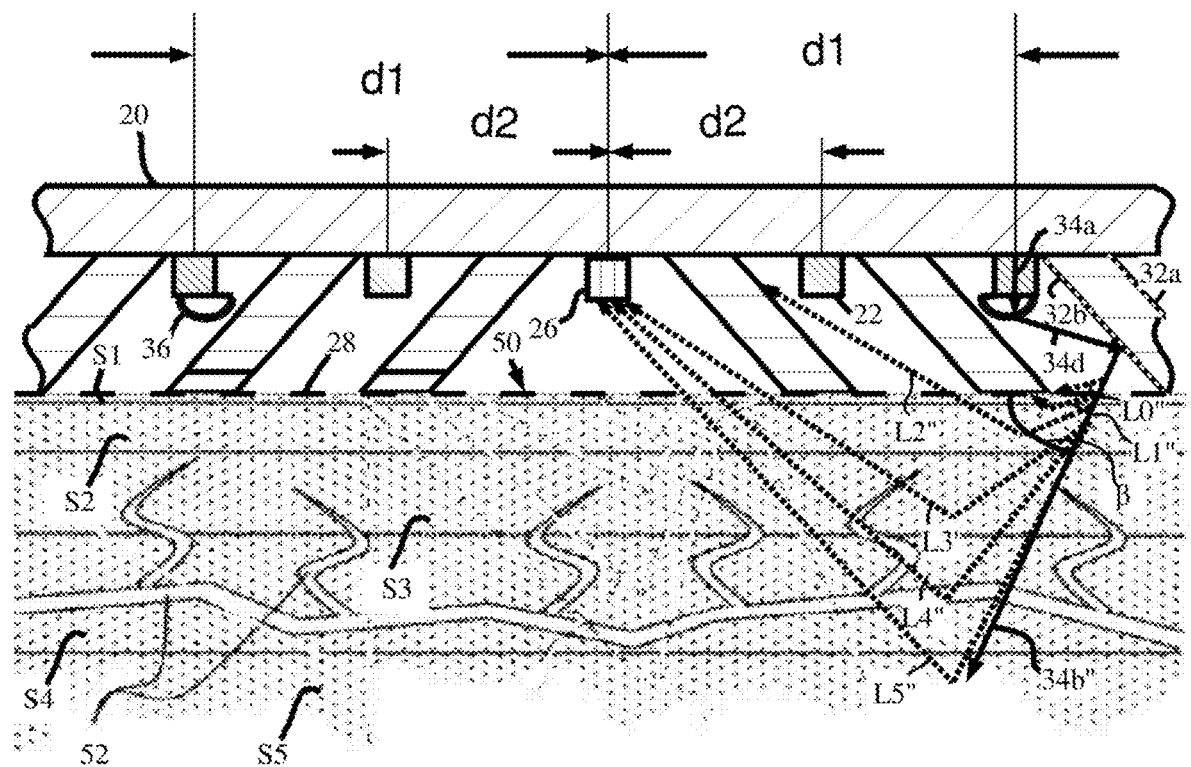
FIG. 5c shows a partial cross-sectional side view of a sensor device and its application to a tissue, according to one or more illustrative aspects of the disclosure.

Reference is now made to FIG. 5c which shows a partial cross-sectional side view of sensor device 10 and its application to a tissue 50, according to one or more illustrative aspects of the disclosure. FIG. 5c is similar to FIG. 5a in that one light source located laterally to the right of light detector 26 at a shorter distance d2 when compared to another light source 22 located laterally to the right of light detector 26 at a greater distance d1. In the description that follows, attention is drawn to the light source 22 located laterally to the right of light detector 26 at a greater distance d1 from light detector 26. Light source 22 includes lens 36 which is laterally offset to the left toward light detector 26. Light signal 34a still emanates from light source 22 at an angle perpendicular to the first planar surface of substrate 20.

However, unlike FIG. 5a, lens 36 causes light signal 34a to be collimated into collimated beam 34d. Lens 36 minimizes the spread and/or scattering of the rays of light signal 34a. However, unlike FIG. 5a, collimated beam 34d is not at an angle perpendicular to the first planar surface of substrate 20. Collimated beam 34d is reflected from surface 32b of reflector 24 laterally to the right of light source 22 as reflected light 34b" at an angle β relative to dashed line 28. Angle β may be less acute than angle α because lens 36 is offset laterally towards reflective surface 32a to the left of light source 22. Lens 36 may also include a polarizing filter (not shown) which polarizes collimated beam 34d. Reflector 24 located laterally to the right of light source may also include reflective surface 32a.

Figure 5D:
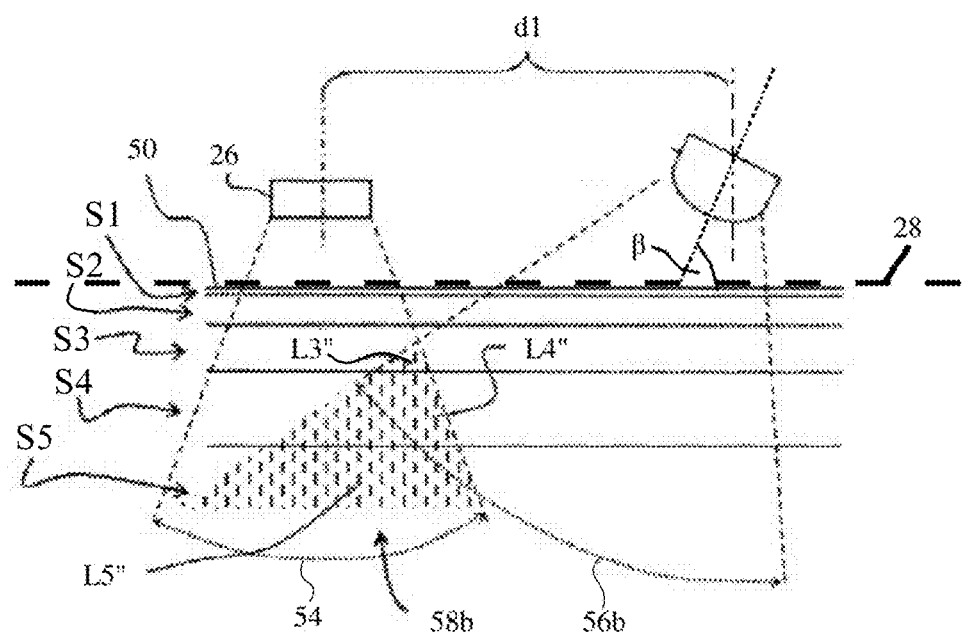
FIG. 5d shows a simplified schematic of FIG. 5c to illustrate features of an area of light interaction in perfused tissue layers, according to one or more illustrative aspects of the disclosure.

Reference is now made to FIG. 5d which shows a simplified schematic of FIG. 5c to illustrate features of an area of light interaction in perfused tissue layers S1-S5, according to one or more illustrative aspects of the disclosure. Area 58b (shown shaded) includes interaction of illumination sector 56b with perfused layers S3-S5 that coincides within a portion of sector 54. Illumination sector Sob is formed by light signal 34b (not shown) reflected off reflector surface 32b as reflected light 34b". Light signals L3", L4" and L5" are reflected towards light detector 26 from perfused tissue layers S3, S4 and S5. Light signals L3", L4" and L5" reflected towards light detector 26. The field of view of reception of received light signals of light detector 26 is indicated by sector 54.

Alternating current (AC) in light detector 26 may be as a result of the light detection of the light wave signals of light 34b" reflected from (capillary) blood vessels 16 which may originate from the heart activity. Where direct current (DC) in light detector 26 may be as a result of the light detection of the light wave signals of light 34b" reflected from other parts of tissue 50 and light wave signals reflected directly from the surface layers S land S2 which do not pass through tissue 50. Light intersection area 58a in perfused tissue layers S3, S4 and S5 is therefore, dependent on angle β relative to dashed line 28, so that light components L3", L4" and L5" are reflected towards light detector 26 from perfused tissue layers S3, S4 and S5. Further, the baseline DC components in the optical signals L0", L1" and L2" measured by the light detector 26 from light intersection area 58b are substantially reduced more than DC components measured by light detector 26 shown by light intersection area 58a. Therefore, light components L3", L4" and L5" reflected towards the light detector 26 may contain significantly more blood related information and contribute greater amounts of pulsating AC components to the optical signals measured by light detector 26.

Figure 5E:
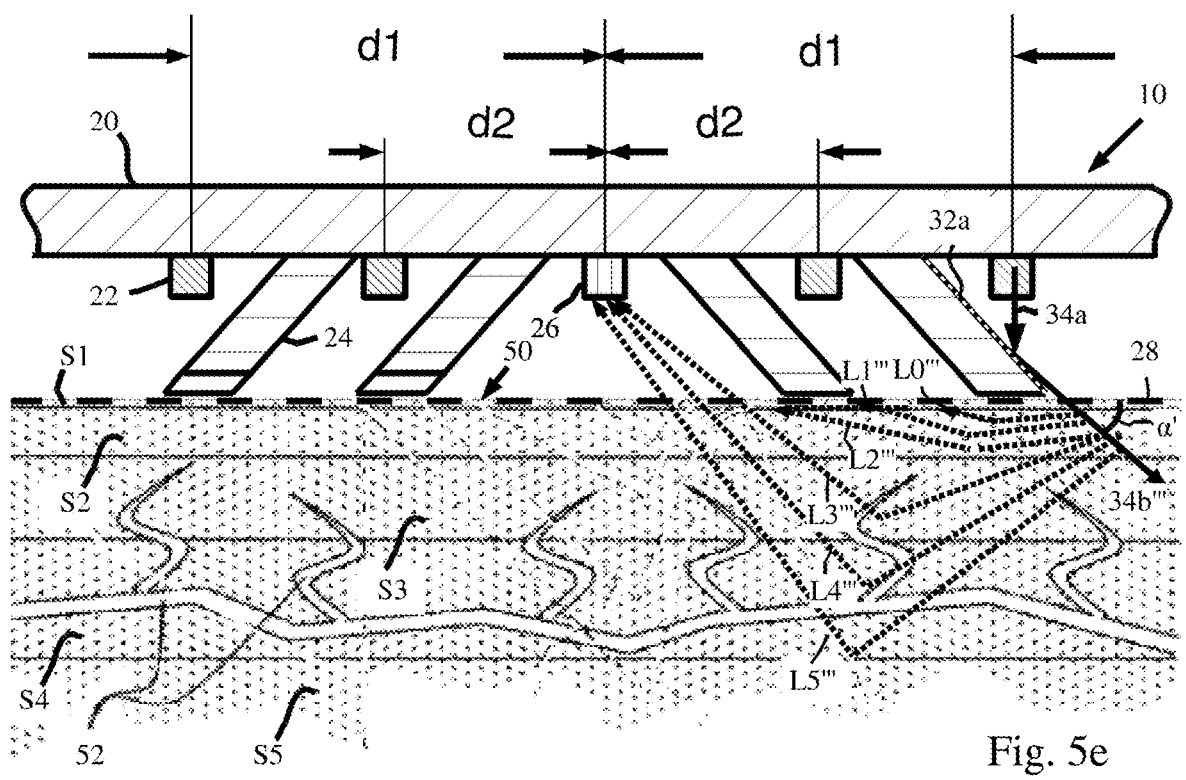
FIG. 5e shows a partial cross-sectional side view of a sensor device and its application to a tissue, according to one or more illustrative aspects of the disclosure.

Reference is now made to FIG. 5e which shows a partial cross-sectional side view of sensor device 10 and its application to a tissue 50, according to one or more illustrative aspects of the disclosure. FIG. 5e is similar to FIG. 5a except one light source 22 is shown with light signal 34a emitted from the one light source 22. The one light source 22 is located laterally to the right of light detector 26 at a longer distance d1 when compared to another light source 22 located laterally to the right of light detector 26 at a shorter distance d2. Light signal 34a from light source 22 is emitted perpendicular to both the first and the second planar surfaces. Light signal 34a is reflected off reflective surface 32a of reflector 24, as reflected light 34b''' at an angle α' relative to dashed line 28.

Angle α' of the orientation of reflected light 34b''' permits light source 22 to be located at a relative long distance d1 in the vicinity of the light detector 26. The relative long distance d1 in the vicinity of light detector 26 may guarantee that the light components L0''', L1''' and L2''' of reflected light 34b''', are reflected from the non-perfused tissue layers S1 and S2 with substantially less acute angles relative to a light direction towards light detector 26 than compared to light components L0', L1' and L2' of FIG. 5a. The light direction towards light detector 26 may be perpendicular to both the first and the second planar surfaces. Thus, the number of light components L0''', L1''' and L2''' reflected from the non-perfused near-surface tissue layers S1 and S2 towards the light detector 26 are reduced to give an improved SNR and AC/DC ratio.

Where alternating current (AC) in light detector 26 may be as a result of the light detection of the light wave signals of light 34b''' reflected from (capillary) blood vessels 16 which may originate from the heart activity. Where direct current (DC) in light detector 26 may be as a result of the light detection of the light wave signals of light 34b''' reflected from other parts of tissue 50 and light wave signals reflected directly from the surface layers S1 and S2 which do not pass through tissue 50. On the other hand, light components L3''', L4''' and L5''' reflect from the remote perfused tissue layers S3, S4 and S5 respectively toward light detector 26, are caused to travel yet greater distances by virtue of locating light source 22 at distance d1 by comparison with locating a light source 22 at shorter distance d2. The greater distances traveled by light components L3''', L4''' and L5''', interact with greater amounts of respective perfused tissue layers S3, S4 and S5 so that the amount of pulsating AC information they contain is substantially increased.

Figure 6:
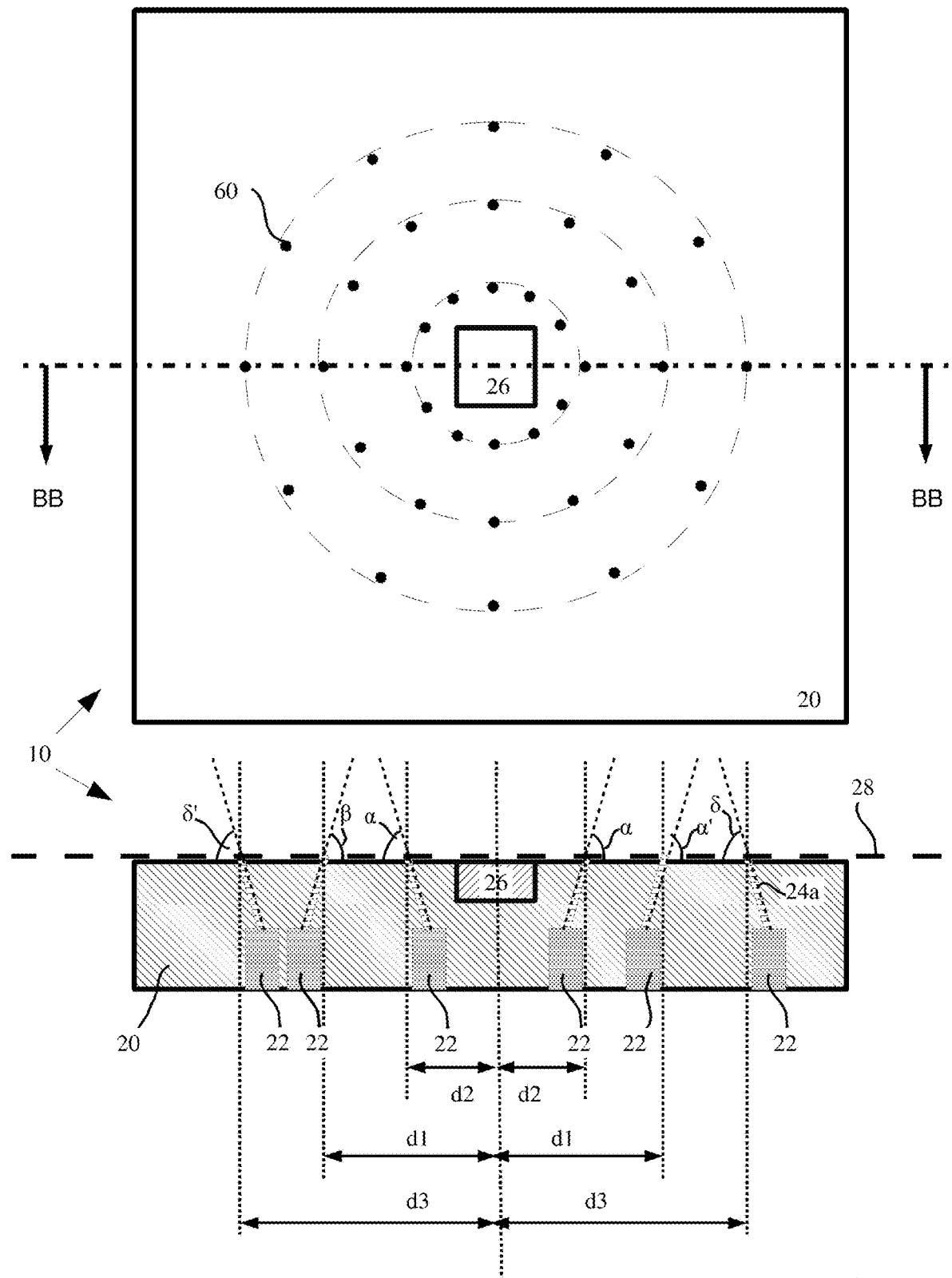
FIG. 6 shows a plan view and a side view cross-section of a sensor device, according to one or more illustrative aspects of the disclosure.

Reference is now made to FIG. 6 which shows a plan view and a side view cross-section BB of sensor device 10, according to one or more illustrative aspects of the disclosure. The plan view shows multiple light apertures 60 placed in substrate 20 located in concentric circles (shown by dashed line) around light detector 26. The side view cross section BB, shows multiple light sources 22 attached both mechanically and electrically in substrate 20. Substrate 20 may further provide an electrical attachment (not shown) to light sources 22 and light detector 26. The electrical attachment may include traces which provide the electrical interconnections of light sources 22 to each other, connections to light detector 26 and additional components. A microcontroller for example may connect to the electrical interconnections as described above with respect to FIG. 4. Light sources 22 and light detector 26 are shown embedded in the surface of substrate 20.

Located and operatively attached between a light source 22 and an aperture 60 is a reflector 24 which may be implemented as a fiber-optic cable. Light emitted from light source 22 may be conveyed through the fiber optic cable from light source 22 to aperture 60 by the total internal reflection (FIR) property of the fiber-optic cable. Substrate 20 may be a non-light transmissive material and may also be made of a material which is rigid enough so as not to be deformed as a result of sensor device 10 being pressed onto an examined tissue. Possible emission of light, controlled by the microcontroller at angle α at distance d2, is shown for two light sources 22 laterally to the left and the right of light detector 26, The operation of the two light sources 22 laterally to the left and the right of light detector 26 is described in detail above with respect to FIGS. 5a and 5b. Possible emission of light, controlled by the microcontroller at angle α' at distance d1, is shown for one light source 22 laterally to the right of light detector 26. The operation of the one light source 22 laterally to the right of light detector 26 is described in detail above with respect to FIGS. 5a, 5b and 5e. Possible emission of light, controlled by the microcontroller at angle β at distance d1, is shown for one light source 22 laterally to the left of light detector 26. The operation of the one light source 22 laterally to the left of light detector 26 is described in detail above with respect to FIGS. 5c and 5d, Additional light sources 22 are shown laterally to the left and right of light detector 26 with possible light emission of angles of δ' and δ respectively.

Light sources 22 may or may not further include lens 36 (not shown) to collimate light signal emanating from a light source 22 into the fiber-optic cable. Lens 36 may be located at the end of the fiber-optic cable and attached to the first planar surface of substrate 20 indicated by dashed line 28. Light sources 22 may or may not further include a polarizing filter (not shown) to polarize collimated light signal and/or light signal from light sources 22. A polarizing filter (not shown) may mounted on the first planar surface of substrate 20 indicated by dashed line 28.

Figure 7:
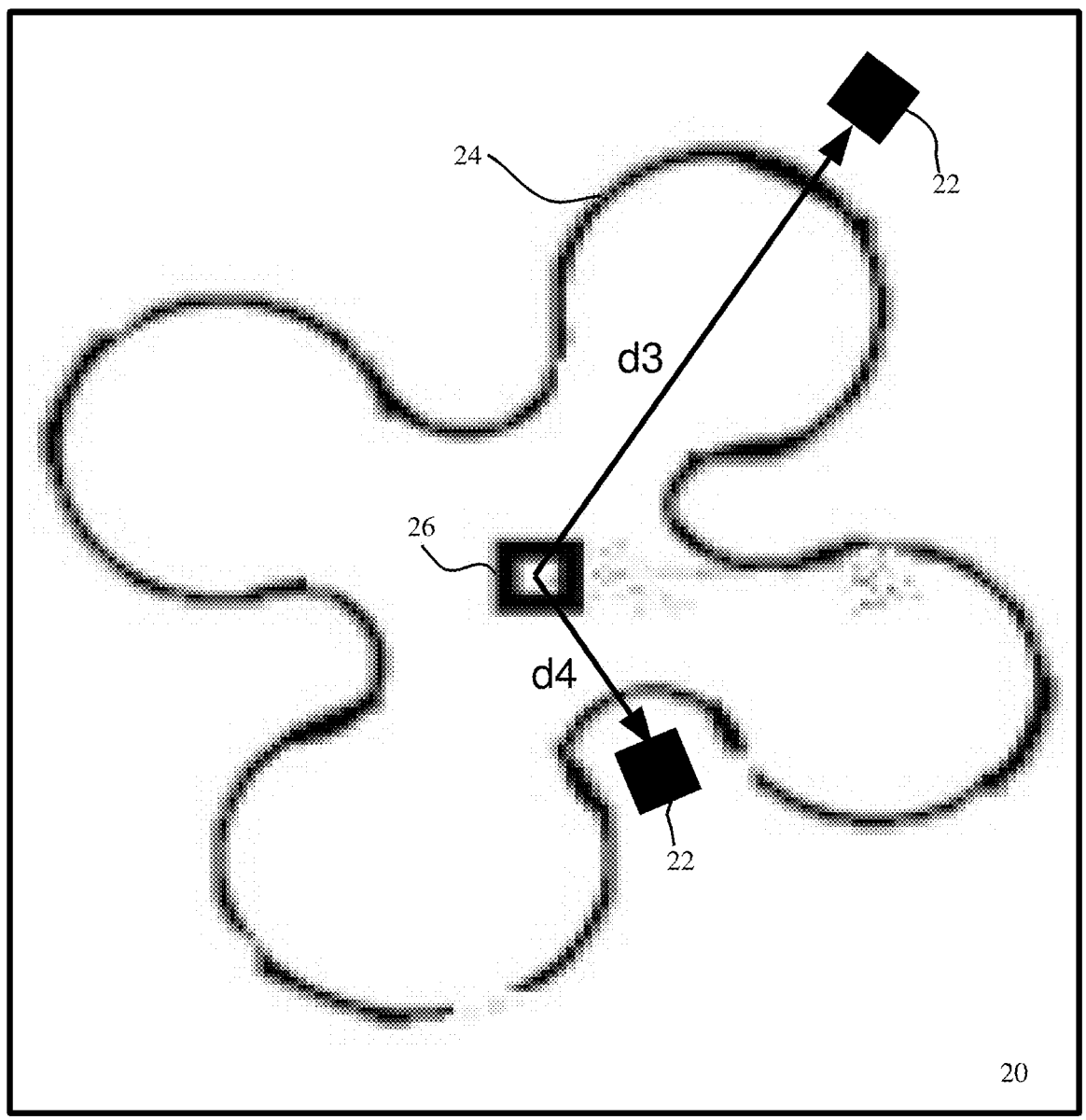
FIG. 7 shows a plan view of a sensor device, according to one or more illustrative aspects of the disclosure.

Reference is now made to FIG. 7 which shows a plan view of sensor device 10, according to one or more illustrative aspects of the disclosure. The plan view shows a clover leaf shape for reflector 24. Similar to FIG. 4, multiple clover leaf shape reflectors 24 may be located concentric to each other with reference to the center of the first planar surface of substrate 20 where light detector 26 is located. Two light sources 22 are shown at respective distances d3 and d4, however, multiple light sources may be located at other parts of the clover leaf shape for reflector 24 and similarly with the multiple clover leaf shape reflectors 24. A side cross section of the clover leaf shape for a reflective surface of reflector 24 such as linear, convex, concave or parabolic as shown in FIGS. 3a-3c and 3f.

Figure 8:
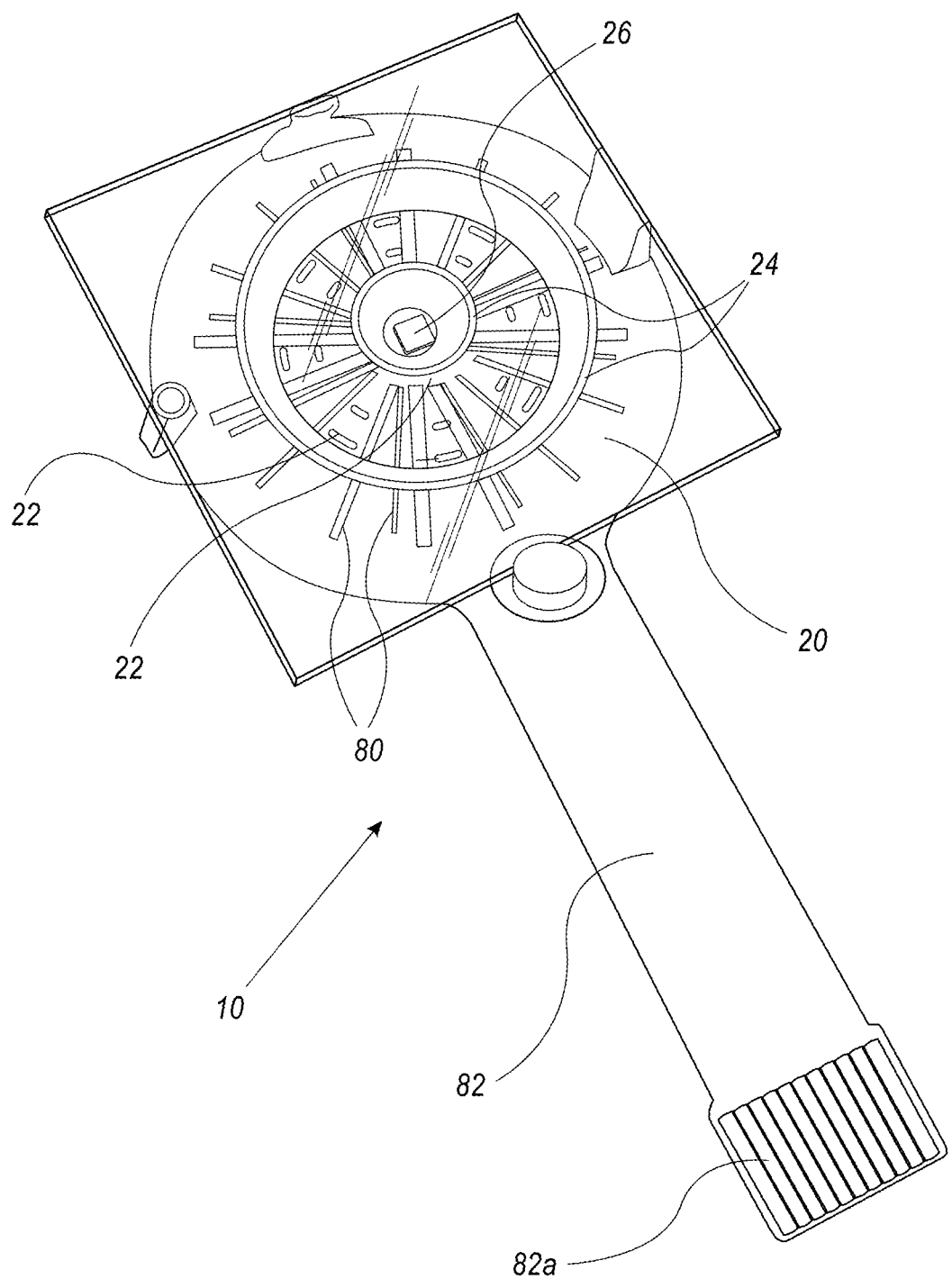
FIG. 8 shows a plan view of a sensor device, according to one or more illustrative aspects of the disclosure.

Reference is now made to FIG. 8 which shows a two-dimensional drawing of the underside of sensor device 10, according to one or more illustrative aspects of the disclosure. Substrate 20 is shown with two reflectors 24 mechanically attached to substrate 20. The two reflectors 24 are concentric to each other. Light detector 26 is located in the center of the smaller reflector 24 and attached both mechanically and electrically to traces 80. Light sources 22 similarly attach both mechanically and electrically to traces 80. Traces 80 provide the interconnections between light sources 22 and control lines to driver circuitries associated with each light source 22. Ribbon cable 80 is attached both mechanically and electrically to substrate 20 and provides a connection port 82a. Connection port 82a provides a connection to traces 80. The connection may allow further electrical connections to a microprocessor and/or display 13 as described above. Sensor device 10 may be housed in housing 12 as shown in FIG. 1.

It is note that the reflective measurement techniques disclosed herein are also very useful for portable as the improved SNR and AC/DC ratios they provide mitigates signals distortions that are induced in the measured signals due to movements of the body part/organ to which the device is attached.

The structure of the invention enables emission of various wavelengths and measurements of various properties. Some wavelengths are reflected differently from the same examined tissue. Hence, the invention also disclosed selecting an optimal combination of angle between the light emitter and light detector as well as the distance between them.

As described hereinabove and shown in the associated Figs., the invention provides a structure to enable reflective measurement configurations for measuring biological properties of an examined tissue/subject with substantially improved SNR and AC/DC: ratios. While particular embodiments of the invention have been described, it will be understood, however, that the invention is not limited thereto, since modifications may be made by those skilled in the art, particularly in light of the foregoing teachings. As will be appreciated by the skilled person, the invention can be carried out in a great variety of ways, employing more than one technique from those described above, all without exceeding the scope of the invention.

What is claimed is:

1. A device, the device comprising:
    a substrate including a connection port, wherein the substrate includes traces to enable a circuit of the substrate, wherein the circuit is connected to the connection port;
    a light sensor mechanically and electrically attached respectfully to a first planar surface of the substrate and the circuit;
    a light source, wherein the light source is mechanically and electrically attached respectively to the first planar surface and the circuit, wherein the light source is located lateral to the light sensor at a first distance, wherein a light signal of the light source emanates from the light source at an angle perpendicular to the first planar surface; and
    a reflector mechanically attached to the first planar surface and located between the light sensor and the light source, wherein the light signal is substantially reflected by the reflector away from the light sensor.

2. The device of claim 1, wherein a profile of a cross section of the reflector surface perpendicular to the first planar surface is at least one of a linear profile, a concave profile, convex profile and a parabolic profile.

3. The device of claim 1, wherein the first distance between the light sensor and a light source is established responsive to the contours of the reflector surrounding the light sensor.

4. The device of claim 1, wherein the light source includes a lens configured to collimate the light signal of the light source at an angle perpendicular to the first planar surface.

5. The device of claim 1, wherein the light source includes an offset lens configured to collimate the light signal of the light source at a second angle away from an angle perpendicular to the first planar surface.

6. The device of claim 1, wherein the light source includes a lens configured to polarize the light signal of the light source at a third angle perpendicular to the first planar surface.

7. The device of claim 1, wherein the light source includes a prism configured to reflect the light signal of the light source at an angle perpendicular to the first planar surface.

8. The device of claim 2, further comprising:
    a second reflector, wherein the second reflector surrounds the reflector;
    a second light source, wherein the second light source is mechanically and electrically attached respectively to the first planar surface and the circuit, wherein a second light signal of the second light source emanates from the second light source at an angle perpendicular to the first planar surface, wherein the second light signal is substantially reflected by the second reflector away from the light sensor, wherein a second distance between the light sensor and the second light source is established responsive to the contours of the second reflector.

9. The device of claim 8, wherein a profile of a cross section of the second reflector surface perpendicular to the first planar surface is at least one of a linear profile, a concave profile, convex profile and a parabolic profile.

10. The device of claim 1, wherein a profile of a cross section of the reflector perpendicular to the first planar surface is at least one of a linear profile, a concave profile, convex profile and a parabolic profile.

11. The device of claim 1, wherein a second planar surface of the reflector is placeable on an examined tissue to measure a biological property of an examined tissue, wherein the second planar surface is parallel to the first planar surface.

12. The device of claim 11, further comprising an attachment device to enable attachment of the device to the examined tissue, wherein the examined tissue is in contact with the second planar surface of the reflector.

13. The device of claim 8, further comprising a control unit operatively connected to the substrate and configured to select a parameter of at least one of the light signal or the second light signal applied to the examined tissue, wherein the parameter is at least one of a wavelength and light intensity.

14. The device of claim 13, wherein the control unit is configured to:
- select and apply at least one of the light signal or the second light signal to the examined tissue;
- sense from the examined tissue, a reflected light signal from at least one of the light signal and the second light signal applied responsive to at least one of the parameter and respective first and second distances; and
- receive and process a measurement data of the reflected light signal sensed by the light sensor to determine the biological properties of the examined tissue, wherein the biological properties include at least one of heart rate, oxygen saturation, hemoglobin level, blood pressure, cardiac output, stroke volume, perspiration, glucose/sugar level, bilirubin level and fat level.

* * * * *

UNITED STATES PATENT AND TRADEMARK OFFICE
CERTIFICATE OF CORRECTION

PATENT NO.       : 10,813,578 B1
APPLICATION NO.  : 16/726976
DATED            : October 27, 2020
INVENTOR(S)      : Arik Ben Ishay, Israel Sarussi and Johanan May Page 1 of 1

It is certified that error appears in the above-identified patent and that said Letters Patent is hereby corrected as shown below:

On the Title Page

Item (72)
In the Inventor, the names:
"Arik Ben Ishay, Zoran (IL);
Israel Sarussi, Ganei Tal (IL);
Johanan May, Petach Tikva (IL)"

Should be replaced with:
-- Arik Ben Ishay, Zoran (IL);
Israel Sarussi, Ganei Tal (IL);
Johanan May, Petach Tikva (IL);
Hassid C. Gurgov, Binyamina (IL) --

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*